United States Patent [19]

Wittich et al.

[11] Patent Number: 5,057,114
[45] Date of Patent: Oct. 15, 1991

[54] MEDICAL RETRIEVAL BASKET

[75] Inventors: Gerhard R. Wittich, Portola Valley, Calif.; Scott E. Boatman; Joseph W. Roberts, both of Bloomington, Ind.

[73] Assignee: Cook Incorporated, Bloomington, Ind.

[21] Appl. No.: 584,473

[22] Filed: Sep. 18, 1990

[51] Int. Cl.5 ............................................. A61B 17/22
[52] U.S. Cl. ................................................... 606/127
[58] Field of Search ............... 606/127; 128/772, 657; 604/164, 282

[56] References Cited

U.S. PATENT DOCUMENTS

| | | | |
|---|---|---|---|
| 1,677,671 | 7/1928 | Councill | 606/127 |
| 4,046,150 | 9/1977 | Schwartz et al. | 606/127 |
| 4,590,938 | 5/1986 | Segura et al. | 606/127 |
| 4,611,594 | 9/1986 | Grayhack et al. | 606/127 |
| 4,633,871 | 1/1987 | Shinozuka | 606/127 |
| 4,860,757 | 8/1989 | Lynch | 128/772 |

FOREIGN PATENT DOCUMENTS 3501707  7/1986  Fed. Rep. of Germany ...... 606/127

Primary Examiner—William E. Kamm
Assistant Examiner—Scott R. Akers
Attorney, Agent, or Firm—Richard J. Godlewski

[57] ABSTRACT

A medical retrieval basket having superelastic metallic alloy wires attached to the distal end of an inner elongated member tube for percutaneously capturing and removing calculi from a cavity or duct of a patient. The basket comprises kink-resistant superelastic metallic alloy wires such as nitinol which forms a bulbous shape for capturing calculi therein. The ends of the superelastic wires of the basket extend through the passageway of the inner elongated member tube and are attached to the proximal end of the tube. An outer elongated member tube is percutaneously inserted into the biliary or urinary system. The inner member tube is inserted through the outer member tube into a duct, cavity or organ of the patient. The distal ends of both the inner and outer member tubes have a predetermined longitudinal curvature for controlling the positioning of the basket and the tubes within the patient. A sleeve is provided at the proximal end of the inner member tube for limiting the insertion thereof in the outer member tube.

20 Claims, 2 Drawing Sheets

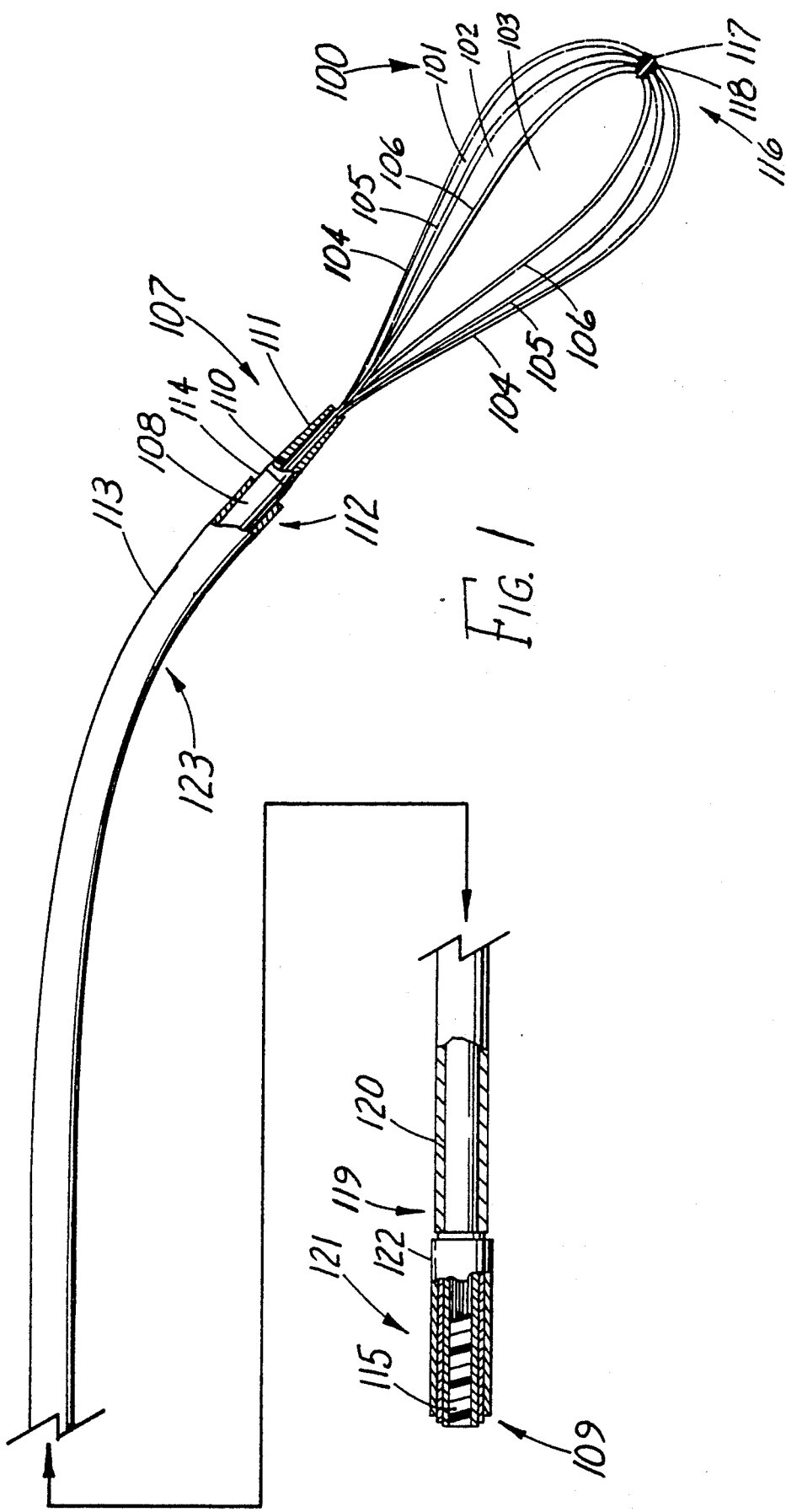

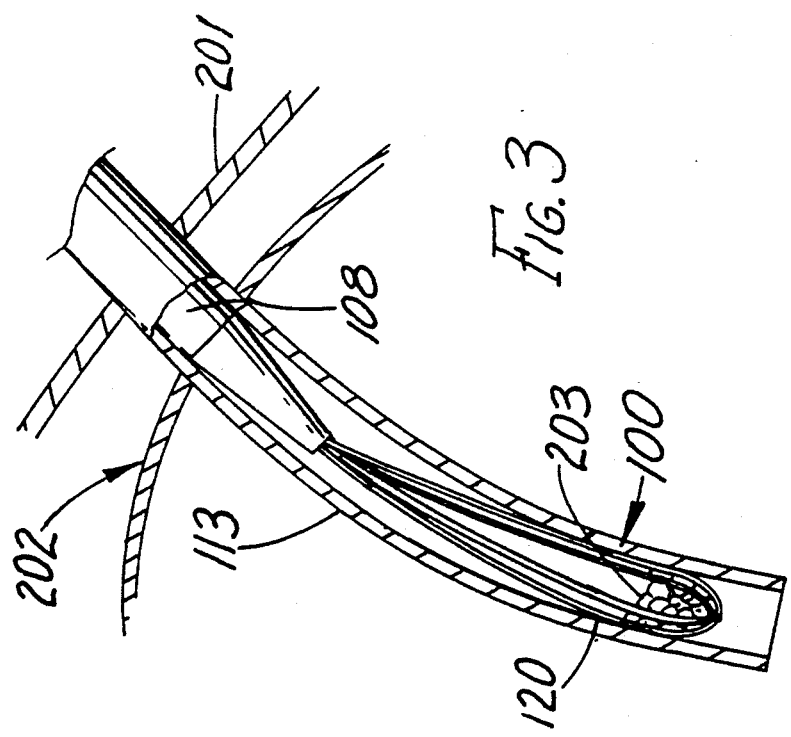
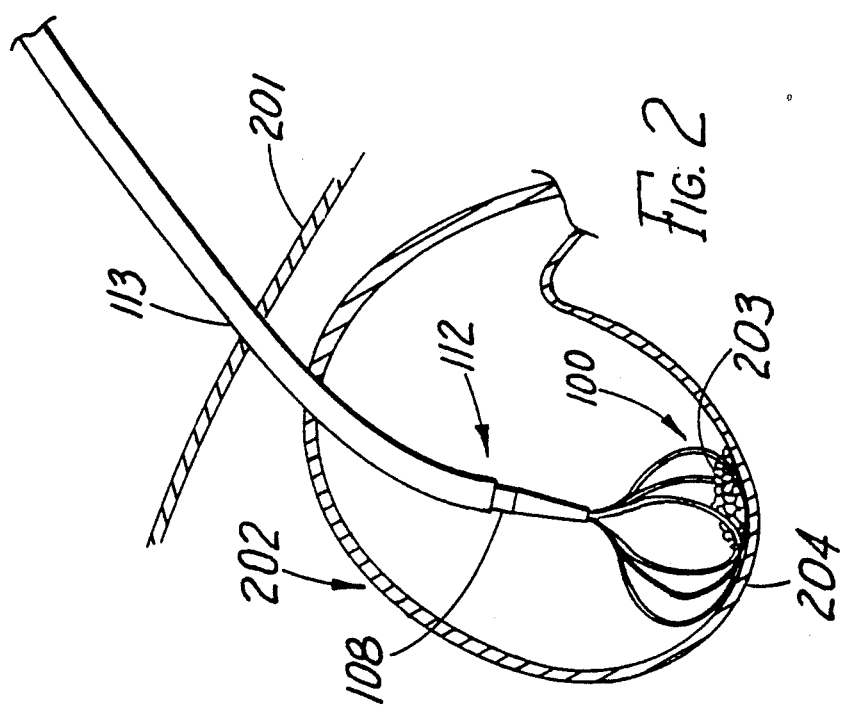

MEDICAL RETRIEVAL BASKET

TECHNICAL FIELD

This invention relates to catheters and, in particular, a stone basket attached to the distal end of a catheter for retrieving calculi and the like from cavities, organs and ducts of the body.

BACKGROUND OF THE INVENTION

Gallstones are a common problem in the United States and the most frequent cause of gallbladder inflammation. Calculi in other parts of the biliary system are also common place as are calculi in the urinary system. Several percutaneous and open surgical procedures are available for removing calculi from the biliary or the urinary system. With respect to the biliary system, one invasive, open surgical procedure is the cholecystectomy in which the gallbladder is removed along with stones from the cystic and common ducts. A T tube is commonly inserted in the common duct for removal of residual calculi. However, such invasive, open surgical procedures are subject to an extensive recovery period lasting from two to six weeks.

Minimally invasive surgical procedures that utilize a percutaneous access include a percutaneous cholecystolithotomy in which calculi are removed through a percutaneously inserted access sheath. Several postoperative access routes such as a transcholedochal, a transcystic duct, a transcholecystic for gallbladder stones and a transcholecystic for choledochal stones are employed for removing biliary stones from the gallbladder, cystic duct, or common duct. In such cases, the extractions are carried out through the fistula tract left by a T tube. The percutaneous extraction is based on the use of forceps or basket-tipped catheters. Forceps enable a quick extraction of stones within reach. Furthermore, forceps facilitate extracting compacted stones. However, forceps are best suited in conjunction with endoscopes to avoid inadvertent extraction of intact mucosa. Another problem with forceps is that they cannot negotiate double or triple curves or the exaggerated tortuosities of fistula tracks. This problem is partially overcome with the basket-tipped catheter which can traverse such winding courses, but it is frequently not possible to seize impacted stones.

A problem with a basket-tipped catheter arises in the case of very small or flat stones particularly when they lie in large cavities where they have ample room for displacement. Most stone extraction baskets are of the helically-shaped variety which permit entry of the stone only from the side of the basket. This is due typically to the tip of the basket, which usually contains a small length of cannula for holding the ends of the wire basket together. Thus, a head-on or an open-ended approach is not possible with these "leading tip" stone retrieval baskets. Helically-shaped baskets also have a tendency to fold on themselves rather to open when pushed against a wall of a hollow organ such as a gallbladder. This reduces the chance of capturing stones. In addition, the relatively sharp tip of such baskets tends to cause an indentation and possible injury of the organ wall.

With presently available open-ended baskets in which the wires of the basket form an open loop to provide a head-on approach, the basket wire is comprised of stainless steel, which is subject to kinking and does not have the desired resiliency for more than one stone capture.

SUMMARY OF THE INVENTION

The foregoing and other problems are solved and a technical advance is achieved by an illustrative stone retrieval basket having a plurality of superelastic alloy wires extending through the passageway of an inner elongated member tube, each wire forming a loop extending longitudinally and distally from the inner member tube. The loops advantageously provide the basket with an open leading end for capturing calculi from body cavities, organs, and ducts. The superelastic basket wire is extremely kink-resistant and permits repeated capture of calculi without kinking.

The retrieval basket comprises inner and outer elongated member tubes each having a hollow passageway extending longitudinally therein. The outer member passageway is for extracting calculi captured within the basket. The basket comprises at least two superelastic alloy wires each having their ends extending through the hollow passageway of the inner member tube and fixedly positioned about the proximal end thereof. Each wire forms a loop extending longitudinally and distally from the inner member tube. The superelastic metallic alloy wire loops are interconnected distally to form the basket.

A fastener such as suture material advantageously interconnects the distal end of the loops. A coating material is also applied to the suture material and the wires at the interconnection to fixedly position the suture material and the wires relative to each other. This fastener also advantageously maintains flexibility for the basket loops to capture calculi with a head-on approach. The coating material prevents the basket loops from sliding at their interconnection.

The basket further comprises a third superelastic metallic alloy wire having ends extending through the passageway of the inner member tube and fixedly positioned about the proximal end of the tube. The third wire forms a third loop extending longitudinally and distally from the distal end and is interconnected distally to the first and second loops.

The superelastic metallic alloy wire of the basket is formed in a bulbous shape approximating that of a light bulb or pear for advantageously capturing calculi particularly in the bottom portion or the flat area of a cavity.

The basket wires illustratively comprise a nickel-titanium alloy such as nitinol, which exhibits a superelastic property when maintained at a temperature above its transformation temperature. The transformation temperature of the superelastic basket wire is selected to be below the normal operating temperature of the basket to maintain the basket wire in a superelastic state. In such state, the superelastic basket wires advantageously return to their original shape when a deformation stress is removed from the wire. The superelastic alloy wire also increasingly resists deformation as the stress load is increased. When nitinol wire is operated below its transformation temperature, heat must be applied to return the alloy wire to its original shape. Advantageously, the operating temperature of the superelastic alloy wire of the present basket is maintained above its transformation temperature to resist kinking and to return to its original shape without the application of any heat thereto.

The inner and outer elongated member tubes of the basket are curved at the distal end thereof to advantageously provide directional control of the outer sheath and basket percutaneously inserted in a cavity, organ, passageway, duct, and the like. The outer member tube comprises a TEFLON material for easy insertion percutaneously into a cavity or duct. The slippery TEFLON material also facilitates the insertion of the inner member tube therein. The inner member tube comprises a polyethylene material and has a predetermined taper at the distal end for extension just beyond the distal end of the outer member tube. The superelastic basket wires are inserted through the passageway of the inner member tube and are attached about the proximal end for insuring that the basket will not dislodge when in the patient. The ends of the wires are attached about the proximal end of the inner member tube and extend through the tube and beyond the distal end thereof. A sleeve comprising a double wall shrink tube is attached about the proximal end of the inner member tube and is larger than the passageway of the outer member tube for advantageously controlling and maintaining the relative positions of the inner and outer tubes with respect to each other. The sleeve also prevents the proximal end of the inner member tube from being inserted into the passageway of the outer member tube.

This basket-tipped catheter is advantageously used both under endoscopic or fluoroscopic control and minimizes the risk of inadvertent damage to mucosa. This basket-tipped catheter also advantageously tends to open when pushed against an organ wall, which significantly reduces the risk of wall damage and increases the chance of capturing stones.

BRIEF DESCRIPTION OF THE DRAWING

FIG. 1 depicts an illustrative stone retrieval basket of the present invention;

FIG. 2 depicts the stone retrieval basket of FIG. 1 percutaneously inserted in a gallbladder;

FIG. 3 depicts the stone retrieval basket of FIG. 1 removing small-sized calculi through the hollow passageway of an outer member tube.

DETAILED DESCRIPTION

Depicted in FIG. 1 is a medical stone retrieval basket 100 comprising three loops 101–103 of respective superelastic metallic alloy wire 104–106. The basket extends from the distal end 107 of an inner elongated member tube 114 for capturing and removing relatively small-sized calculi found in the biliary system. The basket may also break up larger soft stones into smaller pieces which are retrievable with the stone basket. The stone basket is also suitable for use in other cavities, vessels, passages, and organs of the human body such as found in the urinary system and the like. Each of superelastic metallic alloy wires 104–106 comprises a nickel-titanium alloy having a well-known transformation temperature below that of the normal operating environment. In particular, each of superelastic metallic alloy wires 104–106 is comprised of nitinol wire available from Shape Memory Applications, Inc., Sunnyvale, Calif. The transformation temperature of this particular wire is 8° C., which is well below the body temperature of patients in which the wire is inserted for capturing and removing calculi.

Inner elongated member tube 108 has a distal end 107, proximal end 109 and a hollow passageway 110 positioned longitudinally therebetween. Inner elongated member tube 108 comprises a 20 cm length of 8.5 French polyethylene tube having an outer diameter of approximately 0.111 inches and an inner diameter of 0.043 inches. A taper 111 extends from the extreme distal end of the tube for approximately one cm. The full outer diameter of the inner member tube extends beyond the distal end 112 of outer elongated member tube 113 for a short distance 114 of approximately 2 mm.

The ends of superelastic metallic alloy wires 104–106 extend through the entire length of passageway 110 and are attached about the proximal end 109 using an adhesive material 115 such as Loctite Type 454 gel. As the gel is drying, the proximal end of the elongated member tube is heated and compressed radially inward to ensure maximal interface between member tube and wires. The extension of the wires through the passageway of the inner elongated member tube lessens the possibility of the basket from being dislodged and remaining in the cavity or duct of a patient.

By way of example, each of nitinol wires 104–106 comprises a 7 cm length of wire having a 0.010" diameter. The ends of each wire extend through the hollow passageway of the inner elongated member tube. The middle sections of the wire form loops 101–103 extending longitudinally and distally from the inner member tube. The longitudinal length of each loop extending from distal end 107 is approximately 4.5 cm. Each of loops 101–103 forms a bulbous shape such as that of a light bulb or pear.

At distal end 116 of the basket, suture material 117 joins loops 101–103 together. Urethane material 118 coats the suture material and a portion of each wire to fixedly position each loop relative to each other.

Basket 100 and inner elongated member tube 108 are insertable into outer elongated member tube 113 having distal end 112, proximal end 119, and hollow passageway 120 positioned longitudinally therebetween. Outer elongated member tube 113 comprises a 24 cm length of 12 F thick wall TEFLON tube having a 0.158" outer diameter and a 0.116" inner diameter. Distal ends 107 and 112 of respective inner and outer member tubes 108 and 113 have a longitudinal curve 123 with approximately a 1" radius to more easily control and change the direction of the inner and outer elongated member tubes, as well as the basket, when percutaneously inserted in a patient.

Attached about the proximal end 109 of inner elongated member tube 108 is sleeve 121 which acts as a stop and limits the extension of the inner elongated member into the passageway of the outer elongated member tube. Sleeve 121 comprises a 2 cm length of 3/16" diameter double wall shrink tube 122 which is commercially available.

Depicted in FIG. 2 is outer elongated member tube 113 percutaneously inserted through outer tissue layers 201 and into fundus 202 of a gallbladder. The percutaneous insertion of the outer elongated member tube is performed using a well-known radiological procedure. A number of small calculi or gallbladder stones 203 are depicted lying in the lower portion of the gallbladder on wall 204. Inner elongated member tube 108 with basket 100 extending therefrom extends beyond the distal end 112 of the outer elongated tube. The basket is pressed against lower fundus wall 204 to enlarge the bulbous shape of the basket and capture one or more of the small-sized gallbladder stones. The superelastic metallic alloy wire of the basket permits expansion of the bulbous shape to permit either a head-on or side access of calculi into the basket. Furthermore, the bulbous shape permits the basket to be placed directly against the wall of an organ and capture stones positioned thereagainst. The physician rotates and manipulates the basket utilizing the longitudinal curve of the tubes to capture the stones in the basket.

Depicted in FIG. 3 is inner elongated member 108 with several of bladder stones 203 captured in basket 100. The captured stones are being drawn through the passageway 120 of the outer elongated member tube 113. The superelastic metallic alloy wire of the basket does not kink, as would stainless steel wire baskets, and permits the repeated pick up, capture, and removal of small-sized stones within the organ cavity.

It is to be understood that the above-described retrieval basket is merely an illustrative embodiment of the principles of this invention and that other catheters and retrieval baskets extending therefore may be devised by those skilled in the art without departing from the spirit and the scope of this invention. In particular, the basket can be preformed into any desired shape for capturing or removing calculi from the biliary or urinary system. In addition, other semi-rigid materials may be utilized for the inner and outer elongated member tubes to facilitate a variety of different curvatures of the inner and outer elongated member tubes. Furthermore, the nitinol wires have been shown extending to the extreme proximal end of the inner elongated tube for purposes of safety. However, it is contemplated that the basket and wires may also be attached closer to the distal end, if not at the distal end. However, suitably flexible attachment means would be necessary.

What is claimed is:

1. A medical retrieval basket comprising:
   a first elongated member having a proximal end, a distal end, and a first hollow passageway longitudinally positioned therebetween;
   a first superelastic metallic alloy wire having first and second ends extending through said first hollow passageway and fixedly positioned about said proximal end of said first member, said first wire forming a first loop extending longitudinally and distally from said distal end of said first member; and
   a second superelastic metallic alloy wire having first and second ends extending through said first hollow passageway and fixedly positioned about said proximal end of said first member, said second wire forming a second loop extending longitudinally and distally from said distal end of said first member and interconnected distally to said first loop, whereby said said first and second loops interconnected distally form a bulbous shape for atraumatically capturing calculi with a heat-on approach.

2. The basket of claim 1 further comprising a second elongated member having a second distal end, a second proximal end, and a second hollow passageway longitudinally positioned therebetween, said first elongated member and said wires being removably inserted in said second passageway.

3. The basket of claim 1 further comprising a third superelastic metallic alloy wire having first and second ends extending through said first hollow passageway and fixedly positioned about said second proximal end of said first member, said third wire forming a third loop extending longitudinally and distally from said distal end of said first member and interconnected distally to said first and second loops.

4. The basket of claim 3 further comprising a fastener interconnecting distally said first, second, and third loops.

5. The basket of claim 4 wherein said fastener includes a suture interconnecting said first, second, and a third loops.

6. The basket of claim 5 wherein said fastener includes a coating material about said suture and said wires.

7. The basket of claim 1 wherein each of said first and second wires comprises a nickel-titanium alloy.

8. The basket of claim 1 wherein each of said first and second wires comprises nitinol.

9. The basket of claim 2 wherein each of said first and second members has a predetermined longitudinal curve about said distal ends thereof.

10. The basket of claim 8 wherein said second member comprises a TEFLON material.

11. The basket of claim 8 wherein said first member comprises a polyethylene material.

12. The basket of claim 11 wherein said distal end of said first member has a predetermined taper.

13. The basket of claim 2 wherein said first member includes a sleeve attached about said first proximal end and sized larger than said second hollow passageway.

14. The basket of claim 13 wherein said sleeve comprises a double wall shrink tube.

15. A medical retrieval basket comprising:
   a first tube having a first proximal end, a first distal end, and a first passageway longitudinally positioned therebetween;
   a second tube having a second proximal end, a second distal end, and a second passageway longitudinally positioned therebetween and removably inserted in said first tube passageway, said first and second tubes each having a predetermined longitudinal curvature about said distal ends thereof;
   first, second, and third superelastic metallic alloy wires each having a pair of ends extending longitudinally through said second passageway and fixedly positioned therein about said second proximal end, said first, second, and third wires forming respective first, second, and third loops extending longitudinally and distally from said second distal end; and
   a fastener interconnecting said loops distally, whereby said said first and second loops interconnected distally form a bulbous shape for atraumatically capturing calculi with a head-on approach.

16. The basket of claim 15 wherein said tubes are comprised of a polymer material.

17. The basket of claim 15 wherein each of said wires comprises a nickel-titanium alloy.

18. The basket of claim 15 wherein said second tube includes a sleeve positioned about said second proximal end and, sized larger than said first passageway.

19. The basket of claim 15 wherein said sleeve comprises a double wall shrink tube.

20. A medical retrieval basket comprising:
   a TEFLON tube having a first distal end, a first proximal end, and a first passageway extending longitudinally therebetween;
   a polyethylene tube having a tapered distal end, a second proximal end, and a second passageway extending longitudinally therebetween and removably inserted in said first passageway, said second tube having a double wall sleeve attached about said second proximal end and sized larger than first said passageway, said tubes each having a predetermined longitudinal curvature about said distal end thereof;

first, second, and third nitinol wires each having a superelastic state and a pair of ends extending longitudinally through said second passageway and fixedly positioned therein about said second proximal end, said first, second and third wires forming respective first, second and third loops extending longitudinally and distally from said second distal end; and a suture and a urethane coating fixedly interconnecting said loops at a farmost distal position thereof, said first tube passageway being sized for withdrawing said loops in a collapsed state therethrough.

* * * * *